United States Patent [19]

Goldstein et al.

[11] Patent Number: 5,315,004
[45] Date of Patent: May 24, 1994

[54] PROCESS FOR PRODUCING URETIDIONE DIMERS OF ISOCYANATES USING CATALYSTS WHICH ARE BOUND TO INORGANIC MATRICES

[75] Inventors: Stephen L. Goldstein, Cheshire; Anthony D. Hamer, Newtown; Lawrence E. Katz, Orange; Michael J. McGeary, Meriden; Curtis P. Smith, Cheshire, all of Conn.

[73] Assignee: Olin Corporation, Cheshire, Conn.

[21] Appl. No.: 43,075

[22] Filed: Apr. 5, 1993

[51] Int. Cl.$^5$ .................. C07D 229/00; C08G 18/74
[52] U.S. Cl. ............................ 540/202; 548/951; 528/73
[58] Field of Search ............... 548/952; 540/202; 528/73

[56] References Cited

U.S. PATENT DOCUMENTS

| | | | |
|---|---|---|---|
| 3,919,195 | 11/1975 | Bakhitov et al. | 540/202 |
| 4,476,054 | 10/1984 | Disteldorf et al. | 260/239 A |
| 4,912,210 | 3/1990 | Disteldorf et al. | 540/202 |
| 4,929,724 | 5/1990 | Engbert et al. | 540/202 |
| 5,100,998 | 3/1992 | Kopp et al. | 540/202 |
| 5,149,766 | 9/1992 | Bruchmann | 540/202 |

FOREIGN PATENT DOCUMENTS

| | | |
|---|---|---|
| 2049517 | 2/1992 | Canada . |
| 3420113 | 5/1984 | Fed. Rep. of Germany . |

*Primary Examiner*—Mukund J. Shah
*Assistant Examiner*—Pavanaram K. Sripada
*Attorney, Agent, or Firm*—Dale Lynn Carlson

[57] ABSTRACT

This invention relates to a process for preparing a dimer by the steps of: (a) cyclodimerizing a polyisocyanate in the presence of a dimerization catalyst which is covalently bound to an insoluble inorganic matrix by contacting said polyisocyanate with said catalyst at a temperature of between about 20 and about 135° C. in a reaction to form an uretidione-containing cyclodimerized isocyanate wherein a portion of the isocyanate moieties comprising said polyisocyanate are converted to uretidione groups, and (b) separating said catalyst from said cyclodimerized isocyanate in order to stop said reaction after a desired amount of isocyanate moieties in said polyisocyanate have been converted to uretidione moieties.

17 Claims, No Drawings

PROCESS FOR PRODUCING URETIDIONE DIMERS OF ISOCYANATES USING CATALYSTS WHICH ARE BOUND TO INORGANIC MATRICES

FIELD OF THE INVENTION

This invention relates generally to uretidione adducts, and, more specifically, to a process for preparing isocyanate dimers using a catalyst which is covalently bound to an insoluble inorganic matrix.

BACKGROUND OF THE INVENTION

Polyuretidione adducts of polyisocyanates are intermediates which can be used in the preparation of high performance urethane coatings, paints, and films. These adducts provide reduced volatility and an associated reduced toxicity hazard during use, as compared to monomeric polyisocyanates, such as, for example, toluene diisocyanate. In addition, because of their low viscosity, isocyanato uretidiones can be used as reactive diluents for other highly viscous or solid isocyanate group containing coatings components or as a polyisocyanate component in solvent-free and low solvent coatings formulations.

Processes for preparing these adducts are well known. Examples illustrative of these processes can be found in U.S. Pat. Nos. 4,476,054; 4,912,210; and 4,929,724. Generally, the prior art processes involve adding a soluble catalyst which promotes the isocyanate to uretidione (also known as "dimerization") reaction of the precursor isocyanate, optionally in the presence, but usually in the absence, of a solvent, allowing the reaction to proceed to the desired extent and then stopping the reaction with a suitable quenching agent which destroys the activity of the catalyst. Alternatively, in the cases where relatively volatile catalysts are used, the reaction is stopped by distilling the catalyst along with the residual, unreacted precursor isocyanate from the product dimer.

After the residual, unreacted precursor isocyanate is removed, the resulting material, in the case where the precursor isocyanate is a diisocyanate, is a mixture of oligomers composed of 2, 3, 4, etc. precursor diisocyanate molecules joined by 1, 2, 3, etc. uretidione rings. Usually, this mixture is simply called dimer,.

In the case where the precursor isocyanate is polyisocyanate, the reaction is generally stopped well before all the isocyanate groups have been converted to uretidione groups because, otherwise, the resulting product would be an unusable polymer having a very high (theoretically infinite) molecular weight and viscosity. However, the cost of equipment and energy to remove residual, unreacted precursor isocyanate dictate that the reaction not be stopped too soon. Generally, the reaction is run to more than 10% conversion but less than 50% conversion. The preferred range is between 20 and 35%. The reaction is typically stopped using a quenching agent. The reaction between conventional dimerization catalysts and quenching agents typically results in the formation of an insoluble product which is typically removed by filtration using a filter aid.

Unfortunately, both the quenching agent and the filter aid increase the likelihood of introducing undesirable impurities into the product. Accordingly, new processes for producing dimers that do not employ a quenching agent and filter aid(s), and employ fewer process steps than prior art processes, would be highly desired by the dimer manufacturing community. Alternatively, in the cases where relatively volatile catalysts are used: the catalyst is contained in the recovered precursor isocyanate, making it unsuitable for any other use except recycle to the dimerization process; and, because the dimerization reaction is thermally reversible, especially in the presence of a catalyst, some of the product dimer is converted back to precursor isocyanate before the catalyst is removed at elevated temperatures. Accordingly, new processes for producing dimers that provide higher yields of product dimer, as well as catalyst-free recovered precursor isocyanate, would also be highly desired by the dimer manufacturing community.

An approach to meeting this need would be a catalyst that is bound to an insoluble substrate. Such systems are described in German Patent DE 4,026,705 wherein trialkyl phosphines are adsorbed onto matrices with specific surface characteristics. However, this technique suffers from two deficiencies. First, trialkyl phosphines promote the formation of isocyanurates in addition to uretidiones. This results in a higher viscosity product and also makes the product unsuitable for applications wherein cross linked, thermoset, films and elastomers are not desired. Secondly, the phosphine is not chemically bound to the substrate, therefore, some portion of the catalyst remains in solution after the substrate is filtered from the reaction mixture. Consequently, the addition of a catalyst inhibitor is still required before the unreacted isocyanate precursor is removed from the final product. Of course, this product is thereby contaminated with catalyst and inhibitor residues.

A more preferable approach is disclosed for a trimerization process in co-pending U.S. patent application 07/844,265, filed on Mar. 2, 1992 wherein the catalytic site is covalently bound to an insoluble organic polymer, and this process has also been used in dimer production. The described catalyst systems overcome the above cited limitations inasmuch as it is demonstrated that no catalytic residues remain in the product after the resin is removed. Therefore, no catalyst inhibitors need to be added to the product; and, the preferred catalytic site, derived from 4-aminopyridine, exclusively promotes the formation of uretidiones, thereby giving a more desirable product, free of isocyanurates. However, organic polymer substrates have some shortcomings. It is necessary to subject the as-produced resin to a rigorous pretreatment to remove low molecular weight oligomers that would otherwise contaminate the uretidione product. Even with such a pretreatment, moderate, but undesirable, levels of color are formed in the dimerization process. Most problematic is the accumulation uretidione oligomers within the resin during the dimerization reaction. This phenomenon of oligomer fouling continuously reduces the activity of the catalyst resin and thereby limits its single use lifetime. Further, the trapped oligomers can not be easily washed from the substrate. Thus, they represent an undesirable yield loss and necessitate the use of very rigorous conditions to regenerate the catalyst resin for reuse.

While, in principle, the aforementioned problems can be reduced through the use of more highly cross linked ("macroporous" or "macroreticular") polymers, they can not be eliminated as there is still some migration of the precursor isocyanate into the resin. Further, it is difficult to prepare such polymers with practical levels of catalytic sites available on the surface of the resin bead. Thus, a most preferred approach would be embodied in systems wherein the catalytic sites are covalently bound to the surface of an inorganic matrix. In principle, all of the above described problems arising from the dissolution of the precursor isocyanate into the catalytic substrate would be circumvented. Heretofore, such isocyanate dimerization catalyst systems have not been known to the knowledge of the present inventors.

SUMMARY OF THE INVENTION

In one aspect, the present invention relates to a process for preparing a dimer by cyclodimerizing an isocyanate in the presence a dimerization catalyst which is covalently bound to an insoluble inorganic matrix to form an uretidione-containing cyclodimerized isocyanate.

In another aspect, the present invention relates to a process for preparing a dimer by the steps of:

(a) cyclodimerizing a polyisocyanate in the presence a dimerization catalyst which is covalently bound to an insoluble inorganic matrix by contacting said polyisocyanate with said catalyst at a temperature of between about 20° and about 130° C., preferably between about 20° and about 110° C., in a reaction to form an uretidione-containing cyclodimerized isocyanate wherein a portion of the isocyanate moieties comprising said polyisocyanate are converted to uretidione groups, and (b) separating said catalyst from said cyclodimerized isocyanate in order to stop said reaction after a desired amount of isocyanate moieties in said polyisocyanate have been converted to uretidione moieties.

In yet another aspect, the present invention relates to a process for preparing a dimer by cyclodimerizing an isocyanate in the presence a dimerization catalyst which is covalently bound to an insoluble inorganic matrix to form an uretidione containing cyclodimerized isocyanate wherein the dimerization catalyst which is covalently bound to an insoluble inorganic matrix consists essentially of an inorganic substrate and having dimerization catalyst moieties chemically bound to said substrate, said catalyst moieties being selected from the group consisting of: aromatic tertiary amines, especially 4-dialkylamino and 4-(N-arylalkyl-N-alkyl)amino pyridines; alkyl- and alkylamino-phosphines and their derivatives; and combinations thereof.

These and other aspects will become apparent upon reading the following detailed description of the invention.

DETAILED DESCRIPTION OF THE INVENTION

In accordance with the present invention, it has now been surprisingly discovered that dimerization catalysts which are covalently bound to an insoluble inorganic matrix are suitably prepared which are then employed in a straightforward fashion to provide a facile dimerization reaction. The term "dimerization catalyst which is covalently bound to an insoluble inorganic matrix" as used herein is intended to designate bound dimerization catalysts which are insoluble in the dimerization reaction medium by virtue of the inorganic support (also referred to herein as "inorganic substrate" and "inorganic matrix"), and thus are easily separated from the reaction medium by removal of the bound catalyst from the reaction medium after the dimerization reaction has proceeded to the desired extent of completion.

The catalyst composition useful in the process of the present invention comprises an inorganic substrate which is insoluble in the reaction medium and which contains sites that promote the dimerization reaction which are bound to the substrate through ionic or, more preferably, covalent bonds. Compounds which promote the reaction converting isocyanate to uretidione are well known in the art. However, heretofore it was not known to the knowledge of the present inventors whether or not these various reaction promoters would still be active dimerization catalysts when bound to an inorganic substrate to provide a dimerization catalyst which is covalently bound to an insoluble inorganic matrix.

In accordance with the present invention, it has now been found that specific classes of functional groups are suitably employed as dimerization catalysts which are covalently bound to an insoluble inorganic matrix for the desired dimerization reaction. Useful moieties thus include bound derivatives of the following: aromatic tertiary amines, especially 4-dialkylamino and 4-(N-arylalkyl-N- alkyl)amino pyridines; alkyl- and alkylamino-phosphines and their derivatives; and the like. The dialkylamino and 4-(N-arylalkyl-N- alkyl)amino pyridine containing functional groups are preferred because of their enhanced stability in the reaction medium and their ease of regeneration.

The inorganic support for the catalyst should be inert and "essentially insoluble" (i.e., not soluble to any substantial degree) in the dimerization medium. Additional factors to be considered in selecting preferred inorganic supports are: availability; cost; stability; ease of functionalization; particle size; surface area; pore diameter; and, pore volume. Suitable grades of aluminas, carbons, clays, glasses, silicas, and zeolites can be found which provide acceptable performance by many of these criteria. However, matrices composed of aluminum oxides (aluminas), silicon oxides (silicas) and chemical mixtures thereof, are most preferred because of their thermal and chemical stability, and the ease with which they can be functionalized. In addition, aluminas and, especially, silicas with desirable physical characteristics (particle size, surface area, pore diameter, and pore volume) are easily obtained.

The macroscopic form of the substrates that can be employed in the process of this invention can be varied significantly. The substrate can be utilized in the form of beads or powder or other relatively small particles. However, using the catalysts which are covalently bound to an insoluble inorganic matrix in the form of small beads is generally preferred since this simplifies removal of the bound catalyst through filtration and similar such techniques. Useful particle sizes are from 0.01 to 6 mm.

It is generally desirable that the particles of these inorganic matrices have relatively large surface areas available for functionalization. In part, this area is dependant on the average specific pore volume of the substrate particles and therefore it, also, should be relatively large. Useful surface areas are from 5 to 600 $m^2$/gram with pore volumes from 0.5 to 1.2 $cm^3$/gram.

The average pore diameter of these inorganic substrates must be at least large enough to facilitate intimate contact between the precursor isocyanate and the active sites on the inorganic substrate and then allow the resulting uretidione to migrate away from the catalytic site, making the site available for further reaction. Therefore, generally, larger pore diameters are preferred. However, it is possible, by using matrices with relatively smaller pore diameters to limit the formation of higher molecular weight uretidione oligomers. Useful pore diameters are from 5 to 500 nm (50 to 5000 Angstroms).

The catalytically active sites may be bound to the inorganic support using a number of different approaches. The most accessible reactive species on the surface of silica and alumina particles are hydroxyl groups. These can be activated by a number of reagents. For example, they can be treated with hydrochloric or hydrobromic acid to prepare the corresponding surface bearing silicon halide or aluminum halide groups. These, in turn, can be displaced by a number of functional groups, for example, alcohols or alkoxide salts. If these reagents bear the desired catalytic sites or can be further derivatized to bear such sites, bound catalysts, suitably used in the process of the current invention, can be prepared.

However, routes based upon the facile reaction of alkoxysilanes with Al—OH and Si—OH groups, losing alcohol and giving the corresponding Al—O—Si or Si—O—Si bonds are more conveniently practiced. Haloalkyl functionalized silica can be easily prepared by treatment of activated silica with commercially available trialkoxy 3-chloropropyl or 2-(4'(3')-chloromethylphenyl)ethyl silane to give silica bound alkyl or arylalkyl halides. These, in turn, can be converted to catalytically active sites by reaction with, for example, an alkali metal salt of 4-methylaminopyridine or with Grignard reagents derived from, for example, $(R_2N)_2PCl$ or $R_2PCl$, where R is lower alkyl. Thus prepared would be bound catalysts containing 4-dialkylamino pyridine groups, 4-(N-arylalkyl-N-alkyl)amino pyridine groups, alkyl phosphine, or phosphine amide groups, respectively.

Alternatively, it is usually preferable to follow a route where the condensation of the alkoxysilane with the alumina or silica substrate is the last step in the preparation of the bound catalyst. The required alkoxysilanes bearing catalytically active sites can be prepared by the reaction of, for example, trialkoxy 3-chloropropyl or 2-(4'(3')-chloromethyltrialkoxy phenyl)ethyl silane with, for example, an alkali metal salt of 4-methylaminopyridine or with Grignard reagents derived from, for example, $(R_2N)_2PCl$ or $R_2PCl$, where R is lower alkyl. Further, it is usually more preferable to follow a route wherein the alkoxysilyl group is added to a precursor bearing catalytically active sites as the next to last step in the preparation of the bound catalyst. This is conveniently accomplished by a noble metal catalyzed condensation of alkoxyhydrosilanes with an alkene. The required alkenes bearing catalytically active sites can be prepared by the reaction of, for example, 3-chloropropene or 4(3)-chloromethylstyrene with, for example, an alkali metal salt of 4-methylaminopyridine or with Grignard reagents derived from, for example, $(R_2N)_2PCl$ or $R_2PCl$, where R is lower alkyl.

It is also possible to adjust the number of catalytically active sites (i.e., functional groups) bound to the inorganic matrix. From a practical standpoint, the minimum required number of active sites on the catalyst is that amount that provides a "catalytically effective amount", i.e., an amount sufficient to catalyze the dimerization reaction. The upper limit is, in one sense, defined by the composition of the catalyst and the substrate to which it is being bound. This maximum is in practice determined by the amount that provides a catalyst that permits some control over the desired dimerization reaction. Additionally, the active site content of the bound catalyst which provides a practically useful catalyst is also a function of the activity of the catalyst that is bound to the substrate. Generally, it is found that for the types of catalytic species described above, the range of 0.01 to 10 meq of catalytic sites per gram of substrate is preferred, with levels of 0.1 to 5 meq per gram being most preferred.

There are at least two options with respect to the manner in which the precursor isocyanate, optionally in the presence of a solvent, can be contacted with the catalyst, either (a) packed in a cartridge or tube, or (b) dispersed in a stirred reactor. In either case, the system can be operated in batches, e.g., where the system is charged with isocyanate, the reaction is typically run until the desired level of conversion is reached, and then the product is separated from the catalyst by filtration or similar such means. Alternatively, the system can be run as a continuous process wherein isocyanate is continuously added to the system while the product dimer having the desired level of conversion is continuously withdrawn. Potential hardware configurations include: a Continuously Stirred Tank Reactor ("CSTR") with the catalyst dispersed in the isocyanate; a CSTR which serves as a reservoir for the isocyanate/dimer mixture that is repetitively passed, in parallel, through a battery of catalyst packed cartridges, wherein relatively low levels of conversion are achieved in each pass; or a catalyst packed tube, wherein the desired level of conversion is reached in a single pass through the tube.

A range of bound catalyst concentrations may be used in the process of this invention. The factors to be considered in the selection of preferred catalyst concentrations are: the activity of the catalyst being used; the degree of conversion desired; and, the temperature at which the reaction is conducted. Generally, levels between 0.1 and 75 parts of bound catalyst per 100 parts of precursor isocyanate are preferred. Levels between 1 and 50 parts of catalyst per 100 parts of precursor isocyanate are most preferred.

Co-catalysts are optionally and desirably employed in the process of the present invention as a source of active hydrogens for the uretidione formation reactions. The co-catalysts may be any isocyanate reactive hydrogen containing reagents such as amines, alcohols, carbamates, ureas and the like. The preferred co-catalysts are primary and secondary alcohols, such as, for example, methanol, ethanol, 2-propanol, 1,3-dihydroxy-2-hexyl propane, triethylene glycol monomethyl ether, and the like. Preferably, the co-catalyst is employed in an amount of between about 1:1 and about 10:1 molar equivalents based upon the amount of dimerization catalysts which are covalently bound to an insoluble inorganic matrix employed in the process of the present invention.

A range of temperatures may be used in the process of this invention. The factors to be considered in the selection of preferred reaction temperatures are the amount and the activity of the catalyst being used and the degree of conversion desired. Generally, somewhat elevated temperatures are preferred because they drive the reaction at a reasonable rate. Temperatures between 20° and 130° C. are preferred with temperatures between 20° and 110° C. being most preferred.

The time required for the process of this invention is dependent on the temperature, the amount and type of catalyst used and the degree of conversion sought. Generally, it is desirable that a combination of temperature, catalyst activity and catalyst concentration be used that achieves the required level of conversion within a period of 0.5 to 8 hours.

The cyclodimerization reaction is effectively stopped by removal of the catalyst. The catalyst optionally may be deactivated prior to removal. The catalyst is deactivated by the addition of a suitable blocking agent. Such agents react preferentially with the catalytic sites and block further reaction with isocyanate functional groups. Agents such as hydrogen containing acids or salts of such acids that thermally liberate the acid, alkyl halides and the like, are employed in an amount of between about 1:1 and about 10:1 molar equivalents based upon the amount of dimerization catalyst which is covalently bound to an insoluble inorganic matrix employed in the process of the present invention.

Once the reaction mass has been separated from the bound catalyst, most of the unreacted isocyanate monomer, and any optionally used solvent, is preferably removed from the product dimer by evaporation by any convenient means including simple distillation or thin film evaporation at elevated temperatures and atmospheric or, preferably, reduced pressure, followed by a more stringent process for removal of any remaining residual solvent and precursor isocyanate monomer. This final step is preferably accomplished using a wiped film evaporator ("WFE") in which the exposure of the product stream to high temperatures is minimized. The use of WFE is well-known in the art. Briefly, the process involves passing the monomer containing feed through the WFE apparatus at elevated temperatures, 60° to 130° C., preferably between 80° and 120° C., and reduced pressure, 0.01 to 5 mm Hg, preferably between 0.1 and 2 mm Hg. The feed rate is dependant on the heated surface area of the apparatus, but should be slow enough to permit the removal of most of the residual diisocyanate monomer but fast enough to assure that the product is not exposed to high temperatures for an unnecessarily long period of time. At the end of this treatment, the residual monomer content should be less than 0.2%, preferably less than 0.1% by weight of the product.

The process of the present invention is suitably employed in the production of a wide range of isocyanate dimers, including hexamethylene diisocyanate ("HDI") dimer, isophorone diisocyanate ("IPDI") dimer, H$_{12}$MDI dimer, toluene diisocyanate ("TDI") dimer, methylene diphenylene diisocyanate ("MDI") dimer, naphthalene diisocyanate ("NDI") dimer, cyclohexylene diisocyanate ("CHDI") dimer, 1,4-phenylene diisocyanate ("PPD") dimer, bitolyene diisocyanate ("TODI") dimer, xylene diisocyanate ("XDI") dimer, tetramethyl xylene diisocyanate ("TMXDI") dimer, 1,3-bis(isocyanatomethyl) cyclohexane ("H$_6$MDI") dimer, and the like, as well as, mixtures thereof.

The following examples are intended to illustrate, but in no way limit the scope of, the present invention.

EXAMPLE 1

(A) Preparation of a Silica Bound 4-Bis(3'-methylsilylpropyl)-aminopyridine Catalyst 4-Diallylaminopyridine was prepared by the condensation of 4-chloropyridine with diallylamine, as described by Mathias and Cei (Macromolecules, 1987, 20, 2645). This product was hydrosilylated with diethoxymethylsilane in the presence of chloroplatinic acid, as described by Rubinsztajn, et al, (Macromolecules, 1990, 23, 4026) to yield 4-bis(3'-diethoxymethylsilylpropyl)aminopyridine. Finally, following a procedure similar to that described by Tundo and Venturello (J. Amer. Chem. Soc., 1979, 101, 6606), this product was heated with activated silica (Davison Grade 22, 60-200 mesh, 60 Angstrom, 500 m$^2$/gram BET surface area, 0.75 cm$^3$/gram pore volume), to give the silica bound dialkylaminopyridine with the loss of ethanol. After drying in a vacuum oven at 45° C. for 18 hours, this material found to contain 0.6 meq aminopyridine/gram.

(B) HDI Dimerization Test

To 10 gm of the above silica bound catalyst was added 100 gm HDI. The mixture was stirred and heated at 60°-700° C. for 6 hours. An IR spectrum of the liquid showed that at least 15% of the HDI had been converted to dimer. No absorptions due to isocyanurates were detected.

(C) TDI Dimerization Test

To 1.0 gm of the above silica bound catalyst was added 15 gm TDI (composed of 80% 2,4-TDI and 20% 2,6-TDI). The mixture was stirred and heated at 65° C. for 15 minutes. An IR spectrum of the liquid showed that at least 10% of the TDI had been converted to dimer. No absorptions due to isocyanurates were detected.

(D) IPDI Dimerization Test

To 1.0 gm of the above silica bound catalyst was added 15 gm IPDI. The mixture was stirred and heated at 60°-62° C. for 6 hours. An IR spectrum of the liquid showed that at least 20% of the IPDI had been converted to dimer. No absorptions due to isocyanurates were detected.

EXAMPLE 2

(A) Dimerization Test—Stopping the Reaction

To 30 gm of the silica bound catalyst, prepared in Example 1A, was added 134.4 gm HDI. The mixture was stirred and heated to 70°-75° C. for approximately 4 hours. At this point an IR spectrum of the liquid showed that 18% of the HDI had been converted to dimer. The mixture was filtered under nitrogen through a sintered glass filter funnel. About 100 ml of the filtrate was then heated to 70°-75° C. for 4 hours. During the heating period and at the end the IR spectra showed no increase or decrease in dimer concentration (18%).

(B) Dimerization Test—Continuing the Reaction

To 30 gm of the silica bound catalyst, prepared in Example 1A, was added 117.3 gm HDI. The mixture was stirred and heated to 70°-75° C. for approximately 4 hours. At this point an IR spectrum of the liquid showed that 22% of the HDI had been converted to dimer. Most of the supernatant liquid (97.6 gm) was decanted from the catalyst and 102.7 gm fresh HDI was added. This mixture was heated at 70°-75° C. for 4 hours. An IR spectrum of the liquid showed that 24% of the HDI had been converted to dimer. This process of decanting the supernatant liquid, adding fresh HDI and then heating was repeated an additional two times with no apparent loss in activity of the catalyst.

EXAMPLE 3

To a 1 L flask equipped with a mechanical stirrer, thermometer, nitrogen inlet and a condenser was added 500 gms of HDI and 100 gms of the silica bound catalyst prepared in Example 1A. The mixture was heated and stirred at 80° C. for 6 hours. An IR spectrum of the liquid showed that 25% of the HDI had been converted to dimer. Most of the supernatant liquid (406 gms) was siphoned from the catalyst using a filter stick and 450 gms of fresh HDI were added. The mixture was heated and stirred at 80° C. for 6 hours. An IR spectrum of the liquid showed that 23% of the HDI had been converted to dimer. This process of removing the supernatant liquid, adding fresh HDI and then heating was repeated an additional four times with no apparent loss in activity of the catalyst.

The product fractions were combined and stripped of residual monomer using a wiped film evaporator. The resulting product weighed 614.5 grams, had a color value of 55 APHA and its IR spectrum showed no absorptions due to isocyanurates. The viscosity of the product was 60 cps at 25° C.

EXAMPLE 4

(A) Preparation of an Alumina Bound 4-Bis(3'-methylsilylpropyl)-aminopyridine Catalyst Following a procedure similar to that described by Tundo, et al, (J. Amer. Chem. Soc., 1982, 104, 6547), 4-bis(3'-diethoxymethylsilyl-propyl)aminopyridine, as prepared in Example 1A, was heated with activated alumina (Aldrich 26,774-0, 150 mesh, 58 Angstrom, 155 $m^2$/gram BET surface area), to give the alumina bound dialkylamino-pyridine. After drying in a vacuum oven at 45° for 18 hours, this material was found to contain 0.2 meq aminopyridine/gram.

(B) Dimerization Test

To 40 gm of the above alumina bound catalyst was added 100 gm HDI. The mixture was stirred and heated at 70°–80° C. for 6 hours. An IR spectrum of the liquid showed that at least 15% of the HDI had been converted to dimer. No absorptions due to isocyanurates were detected.

EXAMPLE 5

(A) Preparation of a Silica Bound 4-N-(4'(3')-(2-silylethyl)benzyl)-N-methylaminopyridine Catalyst 4-N-(4'(3')-vinylbenzyl)-N-methylaminopyridine was prepared by the condensation of 4(3)-vinylbenzylchloride with the sodium salt of 4-methylamino pyridine, as described by Tomoi, et al, (Macromol. Chem. Rapid Commun., 1982, 3, 537). This product was hydrosilylated with triethoxysilane in the presence of chloroplatinic acid and BHT, in a procedure similar to that described by Rubinsztajn, et al, (Macromolecules, 1990, 23, 4026) to yield 4-N-(4'(3')-(2-triethoxy-silylethyl)benzyl)N-methylaminopyridine. Finally, following a procedure similar to that described by Tundo and Venturello (J. Amer. Chem. Soc., 1979, 101, 6606), this product was heated with activated silica (Davison Grade 22, 60–200 mesh, 60 Angstrom, 500 $m^2$/gram BET surface area, 0.75 $cm^3$/gram pore volume), to give the silica bound arylalkyl-alkyl-aminopyridine with the loss of ethanol. After drying in a vacuum oven at 45° C. for 18 hours, this material found to contain 0.4 meg aminopyridine/gram.

(B) Dimerization Test

To 35 gm of the above silica bound catalyst was added 100 gm HDI. The mixture was stirred and heated at 70°–80° C. for 6 hours. An IR spectrum of the liquid showed that at least 20% of the HDI had been converted to dimer. No absorptions due to isocyanurates were detected.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. A process for preparing a dimer by cyclodimerizing an isocyanate, in the presence a dimerization catalyst which is covalently bound to an insoluble inorganic matrix substrate, to form an uretidione-containing cyclodimerized isocyanate.

2. The process of claim 1 wherein said dimerization catalyst which is covalently bound to an insoluble inorganic matrix consists essentially of an inorganic substrate and having dimerization catalyst moieties chemically bound to said substrate, said catalyst moieties being selected from the group consisting of: aromatic tertiary amines, alkyl- and alkylamino-phosphines; and combinations thereof.

3. The process of claim 1 wherein said dimerization catalyst which is covalently bound to an insoluble inorganic matrix substrate comprises nitrogen-containing or phosphorus-containing catalytically active sites, or a combination thereof.

4. The process of claim 1 wherein said bound dimerization catalyst comprises a tertiary amine.

5. The process of claim 1 wherein said bound dimerization catalyst a number of functional groups in an amount of between about 0.01 and about 10 milliequivalents of catalytic sites per gram of inorganic substrate.

6. The process of claim 1 wherein said bound dimerization catalyst is employed in an amount of between 0.1 and 50 parts of catalyst per 100 parts of said isocyanate.

7. The process of claim 1 wherein said cyclodimerizing is effected in the presence of a co-catalyst being a primary or secondary alcohol employed in an amount of between about 1:1 and about 10:1 molar equivalents based upon the amount of polymer-bound catalyst employed.

8. A process for preparing a dimer by the steps of:
(a) cyclodimerizing a polyisocyanate in the presence a dimerization catalyst which is covalently bound to an insoluble inorganic matrix by contacting said polyisocyanate with said catalyst at a temperature of between about 20° and about 130° C. in a reaction to form an uretidione-containing cyclodimerized isocyanate wherein a portion of the isocyanate moieties comprising said polyisocyanate are converted to uretidione groups, and
b) separating said catalyst from said cyclodimerized isocyanate in order to stop said reaction after a desired amount of isocyanate moieties in said polyisocyanate have been converted to uretidione moieties.

9. The process of claim 8 wherein said dimerization catalyst which is covalently bound to an insoluble inorganic matrix consists essentially of an inorganic substrate and having dimerization catalyst moieties chemically bound to said substrate, said catalyst moieties being selected from the group consisting of: aromatic tertiary amines, alkyl- and alkylamino-phosphines; and combinations thereof.

10. The process of claim 8 wherein said dimerization catalyst which is covalently bound to an insoluble inorganic matrix comprises nitrogen containing or phosphorus containing catalytically active sites, or a combination thereof.

11. The process of claim 8 wherein said bound dimerization catalyst comprises a tertiary amine.

12. The process of claim 8 wherein said bound dimerization catalyst a number of functional groups in an amount of between about 0.01 and about 10 milliequivalents of catalytic sites per gram of inorganic substrate.

13. The process of claim 8 wherein said bound dimerization catalyst is employed in an amount of between 0.1 and 50 parts of catalyst per 100 parts of said isocyanate.

14. The process of claim 8 wherein said cyclodimerizing is effected in the presence of a co-catalyst being a primary or secondary alcohol employed in an amount of between about 1:1 and about 10:1 molar equivalents based upon the amount of polymer-bound catalyst employed.

15. A process for preparing a dimer by cyclodimerizing an isocyanate in the presence a dimerization catalyst which is covalently bound to an insoluble inorganic matrix to form an uretidione-containing cyclodimerized isocyanate wherein said dimerization catalyst which is covalently bound to an insoluble inorganic matrix consists essentially of an inorganic substrate and having dimerization catalyst moieties chemically bound to said substrate, said catalyst moieties being selected from the group consisting of: aromatic tertiary amines, alkyl- and alkylamino-phosphines; and combinations thereof.

16. The process of claim 15 wherein said insoluble inorganic matrix is selected from the group consisting of aluminas, carbons, clays, glasses, silicas, and zeolites and combinations thereof.

17. A process for preparing a dimer by cyclodimerizing an isocyanate in a reaction medium in the presence a dimerization catalyst which is covalently bound to an insoluble inorganic matrix substrate, said catalyst having between 0.1 and 10 miliequivalents of catalytic sites attributable to said functional groups per gram of said insoluble matrix, and said insoluble inorganic matrix being essentially insoluble in said reaction medium and having a pore diameter of between 5 and 500 nanometer, and a surface area of between 5 and 600 square meters per gram and a pore volume of between 0.5 and 1.2 cubic centimeters per gram of said insoluble inorganic matrix.

* * * * *

UNITED STATES PATENT AND TRADEMARK OFFICE
CERTIFICATE OF CORRECTION

PATENT NO. : 5,315,004
DATED : May 24, 1994
INVENTOR(S) : Stephen L. Goldstein

It is certified that error appears in the above-indentified patent and that said Letters Patent is hereby corrected as shown below:

At column 8, line 14 after "60°-" delete "700°C", and insert --70°C-- in its place.

Signed and Sealed this

Twenty-third Day of August, 1994

Attest:

BRUCE LEHMAN

Attesting Officer

Commissioner of Patents and Trademarks